US006399394B1

(12) United States Patent
Dahm et al.

(10) Patent No.: US 6,399,394 B1
(45) Date of Patent: Jun. 4, 2002

(54) TESTING MULTIPLE FLUID SAMPLES WITH MULTIPLE BIOPOLYMER ARRAYS

(75) Inventors: SueAnn C. Dahm, Palo Alto; Arthur Schleifer, Portola Valley; Carol T. Schembri, San Mateo; Douglas A. Amorese, Los Altos, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/343,645

(22) Filed: Jun. 30, 1999

(51) Int. Cl.[7] .......................... G01N 1/10; G01N 33/48; G01N 21/76; C12M 1/22; B01L 3/00

(52) U.S. Cl. ......................... 436/180; 436/63; 436/172; 435/305.1; 435/305.2; 435/305.3; 422/99; 422/102; 422/104

(58) Field of Search ................................ 422/100, 102, 422/99, 68.1, 104, 105; 436/172, 180, 63; 435/305.1, 305.2, 305.3, 305.4

(56) References Cited

U.S. PATENT DOCUMENTS 4,039,247 A 8/1977 Lawman et al. .............. 350/95
4,237,234 A * 12/1980 Meunier ..................... 435/301
RE30,562 E 3/1981 Park ........................... 435/296
4,315,891 A 2/1982 Sakurada ..................... 422/64
4,319,841 A 3/1982 Suovaniemi et al. ....... 356/244
4,676,951 A 6/1987 Armes et al. ................. 422/65
4,682,891 A 7/1987 de Macario et al. ........ 356/244
4,731,335 A * 3/1988 Brigati ....................... 436/180
4,761,378 A 8/1988 Godsey ...................... 435/293
4,770,856 A * 9/1988 Uthemann et al.
4,798,706 A 1/1989 Brigati ....................... 422/102
4,834,946 A 5/1989 Levin ......................... 422/101
4,877,659 A 10/1989 Vince ........................ 428/34.1
5,061,452 A 10/1991 Yamamoto et al. ......... 422/101
5,104,808 A 4/1992 Laska et al. .................. 436/48
5,120,662 A 6/1992 Chan et al. ................. 436/530
5,126,276 A 6/1992 Fish et al. .................. 436/531
5,143,854 A 9/1992 Pirrung et al. .............. 436/518
5,149,505 A * 9/1992 English et al. ................ 422/99
5,182,191 A 1/1993 Fan et al. .................... 435/7.9
5,213,505 A * 5/1993 Laipply ....................... 434/96
5,436,129 A 7/1995 Stapleton ........................ 435/6
5,482,861 A 1/1996 Clark et al. .................... 436/48
5,508,200 A 4/1996 Tiffany et al. ................ 436/44
5,510,270 A 4/1996 Fodor et al. ................ 436/518
5,538,849 A 7/1996 Uematsu et al. ............... 435/6
5,565,173 A 10/1996 DeWitt et al. .............. 422/131
5,567,595 A 10/1996 Kok .......................... 435/7.92

(List continued on next page.)

FOREIGN PATENT DOCUMENTS

EP 0 118 275 A2 9/1984 ............ C12M/1/20
EP 0 292 995 A2 11/1988 ............ C12M/1/26
WO WO 87/00084 A1 1/1987 ............ B01L/3/00

OTHER PUBLICATIONS

Affymetrix GeneChip® Fluidics Station 400 User's Guide, pp. ii, 5 and 12.

*Primary Examiner*—Jill Warden
*Assistant Examiner*—Brian R. Gordon
(74) *Attorney, Agent, or Firm*—Gordon M. Stewart

(57) ABSTRACT

A method of testing multiple fluid samples with multiple biopolymer arrays. A cover is assembled to a contiguous substrate carrying on a first side, multiple arrays each with multiple regions of biopolymers linked to the substrate, such that the cover and the substrate together form a plurality of chambers each containing a biopolymer array and each being accessible through its own port. Multiple fluid samples are introduced into respective chambers through a port of each such that the fluid samples contact respective arrays. A binding pattern of the arrays is observed. An apparatus and kit useful in such methods, are also provided.

26 Claims, 12 Drawing Sheets

U.S. PATENT DOCUMENTS

| | | | | | |
|---|---|---|---|---|---|
| 5,582,801 | A | | 12/1996 | DeWitt et al. | 422/131 |
| 5,585,275 | A | | 12/1996 | Hudson et al. | 436/518 |
| 5,589,330 | A | | 12/1996 | Shuber | 435/5 |
| 5,591,646 | A | | 1/1997 | Hudson et al. | 436/518 |
| 5,593,642 | A | | 1/1997 | DeWitt et al. | 422/131 |
| 5,593,838 | A | | 1/1997 | Zanzucchi et al. | 435/6 |
| 5,601,141 | A | | 2/1997 | Gordon et al. | 165/263 |
| 5,609,826 | A | * | 3/1997 | Cargill et al. | |
| 5,612,002 | A | | 3/1997 | Cody et al. | 422/131 |
| 5,650,125 | A | | 7/1997 | Bosanquet | 422/102 |
| 5,677,195 | A | | 10/1997 | Winkler et al. | 436/518 |
| 5,679,310 | A | * | 10/1997 | Manns | 422/102 |
| 5,681,484 | A | | 10/1997 | Zanzucchi et al. | 216/2 |
| 5,688,696 | A | | 11/1997 | Lebl | 436/518 |
| 5,702,672 | A | | 12/1997 | DeWitt et al. | 422/131 |
| 5,723,294 | A | | 3/1998 | Glass et al. | 435/6 |
| 5,738,825 | A | * | 4/1998 | Rudigier et al. | 422/82.11 |
| 5,780,294 | A | * | 7/1998 | Stevens et al. | 435/297.5 |
| 5,789,251 | A | * | 8/1998 | Astle | 436/48 |
| 5,801,055 | A | * | 9/1998 | Henderson | |
| 5,817,510 | A | * | 10/1998 | Pandey et al. | |
| 5,858,309 | A | * | 1/1999 | Mathus et al. | 422/102 |
| 6,054,100 | A | * | 4/2000 | Stanchfield et al. | |
| 6,106,783 | A | * | 8/2000 | Gamble | 422/102 |
| 6,136,273 | A | * | 10/2000 | Sequin et al. | 422/99 |
| 6,258,326 | B1 | * | 7/2001 | Modlin | |
| 2001/0007642 | A1 | * | 7/2001 | Feiglin | |

* cited by examiner

TESTING MULTIPLE FLUID SAMPLES WITH MULTIPLE BIOPOLYMER ARRAYS

FIELD OF THE INVENTION

This invention relates to arrays, particularly biopolymer arrays such as DNA arrays, which are useful in diagnostic, screening, gene expression analysis, and other applications.

BACKGROUND OF THE INVENTION

Polynucleotide arrays (such as DNA or RNA arrays), are known and are used, for example, as diagnostic or screening tools. Such arrays include regions (sometimes referenced as spots or features) of usually different sequence polynucleotides arranged in a predetermined configuration on a substrate. The arrays, when exposed to a sample, will exhibit a binding pattern. This binding pattern can be observed, for example, by labeling all polynucleotide targets (for example, DNA) in the sample with a suitable label (such as a fluorescent compound), and accurately observing the fluorescent signal on the array. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated using either in situ synthesis methods or deposition of the previously obtained biopolymers. The in situ synthesis methods include those described in U.S. Pat. No. 5,449,754 for synthesizing peptide arrays, as well as WO 98/41531 and the references cited therein for synthesizing polynucleotides (specifically, DNA). The deposition methods basically involve depositing biopolymers at predetermined locations on a substrate which are suitably activated such that the biopolymers can link thereto. Biopolymers of different sequence may be deposited at different regions of the substrate to yield the completed array. Washing or other additional steps may also be used. Procedures known in the art for deposition of polynucleotides, particularly DNA such as whole oligomers or cDNA, are described, for example, in U.S. Pat. No. 5,807,522 (touching drop dispensers to a substrate), and in PCT publications WO 95/25116 and WO 98/41531, and elsewhere (use of an ink jet type head to fire drops onto the substrate).

In array fabrication, the quantities of DNA available for the array are usually very small and expensive. Sample quantities available for testing are usually also very small and it is therefore desirable to simultaneously test the same sample against a large number of different probes on an array. These conditions require use of arrays with large numbers of very small, closely spaced spots. During use of an array, such as for gene expression monitoring or for patient testing, it will often be desirable to test very large numbers of such small samples against the many of the same or different array patterns. Thus, it is desirable to provide a convenient means by which many samples can be exposed to many arrays in a highly parallel process.

U.S. Pat. Nos. 5,874,219 and 5,545,531 provide a DNA chip wafer to which a plate carrying multiple channels can be mounted, to provide many test wells. Grace Bio-Labs, Inc., of Bend, Oreg., manufactures "Perfusion Chambers" which include covers with openings and which can be placed on specimen slides. However, the present invention appreciates that sample fluid loss can occur in chambers with openings, particularly as a result of evaporation under the elevated temperatures used over a number of hours during hybridizations of nucleic acid arrays. Such losses can potentially result in inaccurate results. Sample contamination may also occur through uncontrolled openings. Furthermore, it may be difficult to provide positive or negative pressure to the chambers to load or empty them while avoiding sample loss. The present invention recognizes that when chambers become very thin to accommodate small sample volumes, capillary forces become significant and some positive means of loading and/or emptying the chamber should preferably be provided which at the same time will avoid sample loss. As well, the present invention recognizes that any closed chamber system for arrays which uses assembled components should be provided with some way of avoiding pushing apart of chamber components as a result of internal pressure increases during heating.

As already mentioned, the testing of multiple samples on multiple arrays on a single substrate has potential to expedite and simplify multiple sample handling. However, such a technique also has the potential to propagate multiple errors. For example, in the case of hybridizing multiple samples to a contiguous substrate carrying multiple polynucleotide arrays, elevated temperatures over a lengthy predetermined time may be required. If for any reason inadequate conditions were provided (for example, by failure of a heating system to reach and maintain the required temperature for the required time), poor results may be obtained. It has been previously disclosed to use control oligonucleotide probes and reference nucleic acid sequences with single arrays. The reference sequences are mixed with sample and the mixture exposed to the array. Hybridization of reference sequences to corresponding reference features, is used as an indication of overall assay performance. However, since sample is present together with reference sequences, there is a potential of interference from similar sequences in a sample. In a conventional situation, where a single sample is tested on a single array, and the inadequate hybridization conditions are not detected, this might lead to a single error. However, with a single substrate carrying multiple arrays, this might suggest system failure and lead to invalidating multiple test results, when the error may in fact be due to interference of the test sample on the hybridization of the reference target to the reference features.

The present invention realizes that it would be desirable then, to provide apparatus and methods for testing multiple samples with multiple arrays, particularly biopolymer arrays such as DNA or RNA arrays, which retain the samples in readily accessible chambers and yet which will not likely suffer sample loss or contamination. The present invention further realizes that it would be desirable that an apparatus and/or method for testing multiple samples with multiple biopolymer arrays, should preferably be able to provide features which include one or more of the following: the ability to allow samples to be positively loaded into or withdrawn from the chamber while avoiding sample leakage; tolerance for increased temperatures without adverse sample loss; of relatively simple constructions; be easy to clean and preferably with any components subject to wear being readily replaceable; and the ability to avoid multiple undetected errors.

SUMMARY OF THE INVENTION

The present invention then, provides in one aspect a method of testing multiple fluid samples with multiple biopolymer arrays. This, or any other aspects of the method, may use any suitable apparatus as described herein. Any of the fluid samples may be of the same or different compositions. The method includes assembling a cover to a contiguous substrate which carries on a first side, multiple arrays each with multiple regions of biopolymers linked to the substrate. As a result, the cover and the substrate together form a plurality of chambers each containing a biopolymer array and each being accessible through its own port. The method further optionally includes introducing multiple fluid samples into respective chambers through a port of each such that the fluid samples contact respective arrays, and observing the binding pattern of the arrays. The binding pattern may be observed in any suitable manner, whether directly or indirectly.

The method may particularly use an apparatus in which each chamber is accessible through a first and a second port. In this case, fluid samples may be introduced into respective chambers through respective first ports while venting through respective second ports. This introduction of multiple fluid samples may optionally be performed simultaneously. The ports may include a resilient self-sealing portion. In this case, the method may additionally include inserting a first set of conduits through the resilient members of respective first ports, and inserting a second set of conduits through the self-sealing portion of respective second ports, with the multiple fluid samples being introduced into each chamber through the first set of conduits while venting occurs through the second set of conduits.

The assembling step of the method may include applying an external force to urge the cover toward the substrate and which remains applied to retain them in the assembled position. By "remains applied" in this context refers to at least remaining applied for one or ten minutes, or at least an hour or multiple hours, and typically refers to remaining applied during manipulations during and following loading of the chambers with samples (for example, including the period following loading during which the temperature may be raised). While many ways of applying and retaining such pressure are possible, a coupler may be used which extends between the cover and the substrate to urge the cover toward the substrate and retain them in the assembled position. The coupler used may be of various configurations, and in one configuration includes a plate with at least one view opening as well as an adjustable interconnect member. With this configuration, the coupler application includes positioning the plate facing a second side of the substrate with the at least one view opening in alignment with the arrays such that the arrays can be observed from the second side of the substrate through the at least one plate view opening. The adjustable interconnect member is extended between the cover and the plate, and adjusted to urge the cover toward the substrate.

In a second aspect of the method of the present invention, a cover is used which includes a cover member and a resilient gasket with multiple openings. These are assembled to a substrate as described above, with the gasket sandwiched between the substrate and cover member and the gasket openings aligned with respective array, such that the cover, substrate, and gasket together form a plurality of chambers. Each of the chambers contains a biopolymer array and is accessible through a port comprising respective port portions of the resilient gasket which normally close the port. The method optionally includes penetrating gasket port portions by at least one conduit and introducing fluid samples into respective chambers through the at least one conduit, such that the fluid samples contact respective arrays. A binding pattern of the arrays may then be observed.

In the second aspect, following assembly the gasket may have a first side facing the substrate and a second side facing the cover member, as well as port portions positioned transversely beyond the substrate. In this configuration, the ports may further include respective fluid ducts in the cover member communicating between respective chambers and respective port portions of the gasket. With this arrangement, the chambers can be accessed by conduits which have penetrated from the first side of the gasket through the port portions to the ducts. The ducts in the second aspect may be of various structures and may, for example, be channels in a first side of the cover member which faces the gasket. Each chamber may again have a first and a second port. The gasket port portions then, act as the resilient self-sealing port portions described above, and can receive conduits therethrough to provide fluid samples and venting in a similar manner as already described. A coupler may be applied between the cover and the substrate, of the same construction and in the same manner as already described.

A third aspect of the methods of the present invention provides a method of testing multiple fluid samples using a contiguous substrate carrying multiple arrays each with multiple regions of biopolymers linked to the substrate. At least one array of the substrate is exposed to a test sample (and optionally, also to a reference sample) under a first set of conditions, and at least one other array is exposed to a reference sample under the same set of conditions. The at least one other array is not exposed to a test sample. This aspect may also include observing a binding pattern of the arrays and, when an observed characteristic of the binding pattern of an array exposed to the reference sample is outside a predetermined limit, either rejecting the binding pattern result for the test sample or modifying observed binding pattern results for the test sample based on a difference between an expected and observed characteristic of an array exposed to the reference sample. Typically (which implies not necessarily) multiple test samples may be exposed to respective arrays. All exposing may or may not be simultaneous. This aspect may optionally further include assembling the cover to the first side of the substrate on which the arrays are carried, such that the cover and the substrate together form a plurality of chambers each containing a biopolymer array and each being accessible through its own port. The multiple test samples and reference sample may be introduced (for example, simultaneously), into respective chambers through a port of each such that the fluid samples contact respective arrays. The binding pattern of the arrays may then be observed. This aspect may optionally further use any of the steps of the other aspects of the methods of the present invention. It will also be appreciated that any additional steps considered desirable, may be used in any aspects of the present method. For example, the methods may optionally additionally include, after applying the coupler, heating the chambers.

In another method of the present invention, the array exposed to the test sample and the array exposed to the reference sample both include at least one reference feature, and wherein both are exposed to at least one reference sequence. These common reference features may, for example, be identical. Similarly, the reference sequence or sequences for each may, for example, also be identical. Again, the binding pattern of the arrays is observed as before. When the binding patterns of the at least one reference feature in both arrays lack a predetermined degree of correlation, the binding pattern result for the test sample is either rejected or an observed binding pattern result for the test sample is modified based on a difference between an expected and observed correlation. In the case of identical reference features in both arrays and the same reference sequence or sequences exposed to each, the predetermined degree of correlation may simply be the predetermined degree of similarity in observed binding at the reference features of both such arrays.

The present invention further provides apparatus of the type which may be used in methods of the present invention. In one aspect, such an apparatus includes a cover defining multiple cavities on a first side and with respective ports communicating with the cavities. The ports include respective resilient self-sealing portions normally closing the ports. The cover can be assembled to a contiguous planar substrate carrying on a first side, multiple arrays each with multiple regions of biopolymers linked to the substrate, such that the cover and the substrate together form a plurality of chambers each containing a biopolymer array and each being accessible through its own port.

The apparatus may optionally further include the foregoing planar substrate attached to the cover, whether permanently (as by bonding with adhesive, welding, or some other means) or releasably (that is, not bonded thereto). In an aspect of the apparatus using a gasket, the gasket may or may not be one which is not adhered to the cover member such that following detachment of the cover from the substrate, the gasket freely detaches from the cover member. The gasket may be of various thickness and may, for example, be sufficiently thick as to define at least 50% (or at least 70% or 80%) of the maximum distance between a substrate and the cover member in the chambers. Also, while the cover member may be of various configurations, it may particularly be a unitary plate, and may further particularly be flat on a first side which faces the substrate when the cover is assembled thereto. By "flat" is meant substantially flat and allowing for irregularities such as the channels therein already described. The cover member may also have guide openings alignable with respective port portions of the gasket. Such a configuration allows the guide openings to facilitate the conduits correctly registering with the port portions of the gasket. While the chambers formed from the cover with a contiguous flat substrate may have various dimensions, the maximum distance between the substrate and the cover in the chambers, defined by the thickness of the gasket, may, for example be no greater than 5 mm (or no greater than 2 mm or 1 mm). The minimum thickness of the gasket may also be within virtually any desired range limited by properties of the material selected. For example, a minimum gasket thickness may be on the order of at least 0.75 mm (or even at least 0.5 mm). Further, the maximum volume of each of the chambers may, for example, be no more than 1000 $\mu$l (or even no more than 500 $\mu$l, 200 $\mu$l or 100 $\mu$l), and may typically be 20 to 200 $\mu$l.

The present invention also provides in a further aspect, a kit for testing multiple fluid samples, comprising a contiguous substrate carrying multiple arrays each with multiple regions of biopolymers linked to the substrate, and a reference sample for exposure to at least one of the arrays. Such a kit may optionally include an instruction that the reference sample is for reference. This instruction may, for example, be in printed, human readable characters on a suitable medium (such as a label adhered to container carrying the reference sample). For example, the instruction might simply be printed as "REFERENCE", "REF" or similar. However, the instructions may include further instructions such that the reference sample is to be exposed to at least one array, or that the reference sample is to be exposed to at least one array under the same set of conditions as at least one test sample being exposed to another array on the same substrate. The kit may, if desired, further include a contiguous substrate carrying multiple arrays each with multiple regions of biopolymers linked to the substrate, and comprising a gasket with multiple openings which are alignable with respective arrays on the substrate.

While the substrates in the aspects of the apparatus, methods and kits of the present invention described above, carry biopolymers, the present invention contemplates that these particular moieties can readily be replaced with other moieties (such as other chemical or biochemical moieties, for example various small molecules) in any of the apparatus, methods or kits of the present invention. Thus, wherever a reference is made to biopolymers, this can be replaced with any such moieties. It will also be appreciated that any of the arrays described, may be the same or different (although often multiple ones, if not all, of the arrays on a substrate will be the same), and may or may not be separated by an intervening space. If there is no intervening space, the gasket may simply cover some areas of biopolymers (which then simply go unused). However, typically the arrays are distinguishable from each other in some manner, such as by an intervening space or by the patterns of the moieties thereon.

The method, apparatus, and kits of the present invention can provide any one or more of a number of useful benefits. For example, the samples exposed to arrays are retained in closed yet readily accessible chambers. Samples can be positively loaded into chambers containing and withdrawn therefrom, under the influence of a slight pressure or vacuum (such as from a syringe) while avoiding sample leakage. Increased temperatures can be well tolerated without generating pressures which could push apparatus components apart and lead to sample loss. The apparatus is relatively simple to construct and, if desired, easy to clean. Components of the apparatus which are particularly subject to wear, such as the resilient gasket at the port portions, is readily replaced while allowing the remainder of the apparatus to be re-used many more times. Further, where a gasket is used chamber volume can be readily altered by using a different gasket. In the case of aspects utilizing a reference, this allows for easy monitoring of error conditions.

BRIEF DESCRIPTION OF THE DRAWINGS

Embodiments of the invention will now be described with reference to the drawings, in which.

To facilitate understanding, the same reference numerals have been used, where practical, to designate similar elements that are common to the figures.

DETAILED DESCRIPTION OF THE INVENTION

Throughout the present application, unless a contrary intention appears, the terms following terms refer to the indicated characteristics. A "biopolymer" is a polymer of one or more types of repeating units. Biopolymers are found in biological systems and particularly include peptides or polynucleotides, as well as such compounds composed of or containing amino acid or nucleotide analogs or non-nucleotide groups. This includes polynucleotides in which the conventional backbone has been replaced with a non-naturally occurring or synthetic backbone, and nucleic acids in which one or more of the conventional bases has been replaced with a synthetic base capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as analogs of such sub-units. Specifically, a "biopolymer" includes DNA (including cDNA), RNA and oligonucleotides, regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution). An "array", unless a contrary intention appears, includes any one or two dimensional arrangement of discrete regions bearing particular biopolymer moieties (for example, different polynucleotide sequences) associated with that region. A "chamber" references an enclosed volume (although a chamber may be accessible through one or more ports). "Venting" or "vent" includes the outward flow of a gas or liquid. It will also be appreciated that throughout the present application, that words such as "upper", "lower" are used in a relative sense only. "Fluid" is used herein to reference a liquid. By one item being "remote" from another is referenced that they are at least in different buildings, and may be at least one, at least ten, or at least one hundred miles apart. Reference to a singular item, includes the possibility that there are plural of the same items present.

Figure 1:
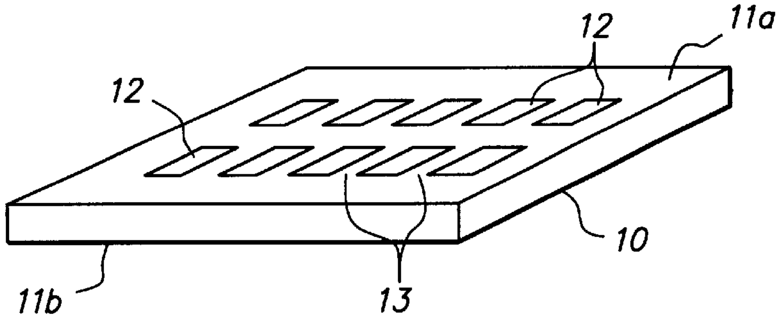
FIG. 1 illustrates a substrate carrying multiple polynucleotide arrays.
Figure 2:
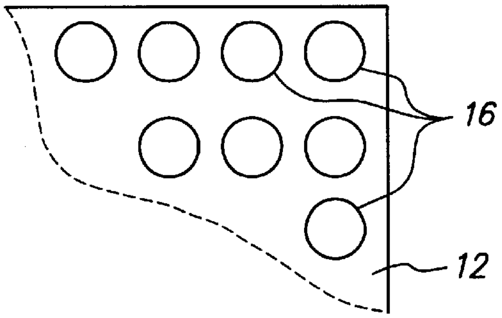
FIG. 2 is an enlarged view of a portion of FIG. 1 showing multiple spots or regions of one array.
Figure 3:
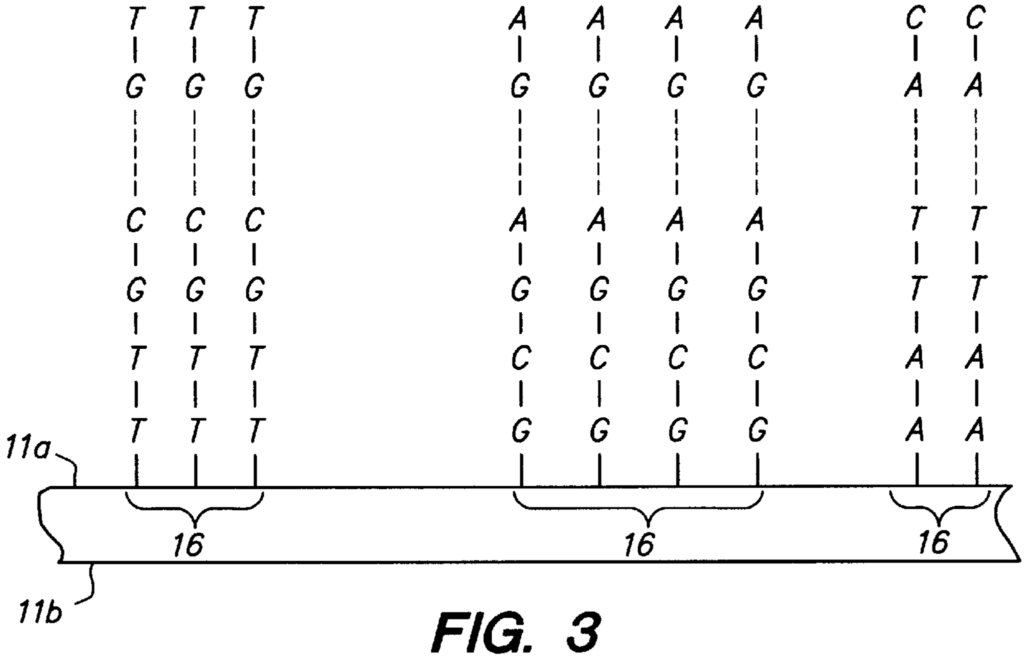
FIG. 3 is an enlarged illustration of a portion of the substrate of FIG. 1.

Referring first to FIGS. 1–3, typically apparatus and methods of the present invention use a contiguous planar substrate 10 carrying multiple arrays 12 disposed across a first surface 11*a* of substrate 10 and separated by areas 13. While ten arrays 12 are shown in FIG. 1 and the different embodiments described below may use substrates with particular numbers of arrays, it will be understood that substrate 10 and the embodiments to be used with it, may use any number of desired arrays 12. Similarly, substrate 10 may be of any shape with the apparatus used with it adapted accordingly. Any of arrays 12 may be the same or different from one another and each will contain multiple spots or regions 16 of biopolymers in the form of polynucleotides. A typical array may contain at least ten regions, or at least 100 regions, at least 100,000 regions, or more. All of the regions 16 may be different, or some or all could be the same. Each region carries a predetermined polynucleotide having a particular sequence, or a predetermined mixture of polynucleotides. This is illustrated schematically in FIG. 3 where regions 16 are shown as carrying different polynucleotide sequences.

Figure 4:
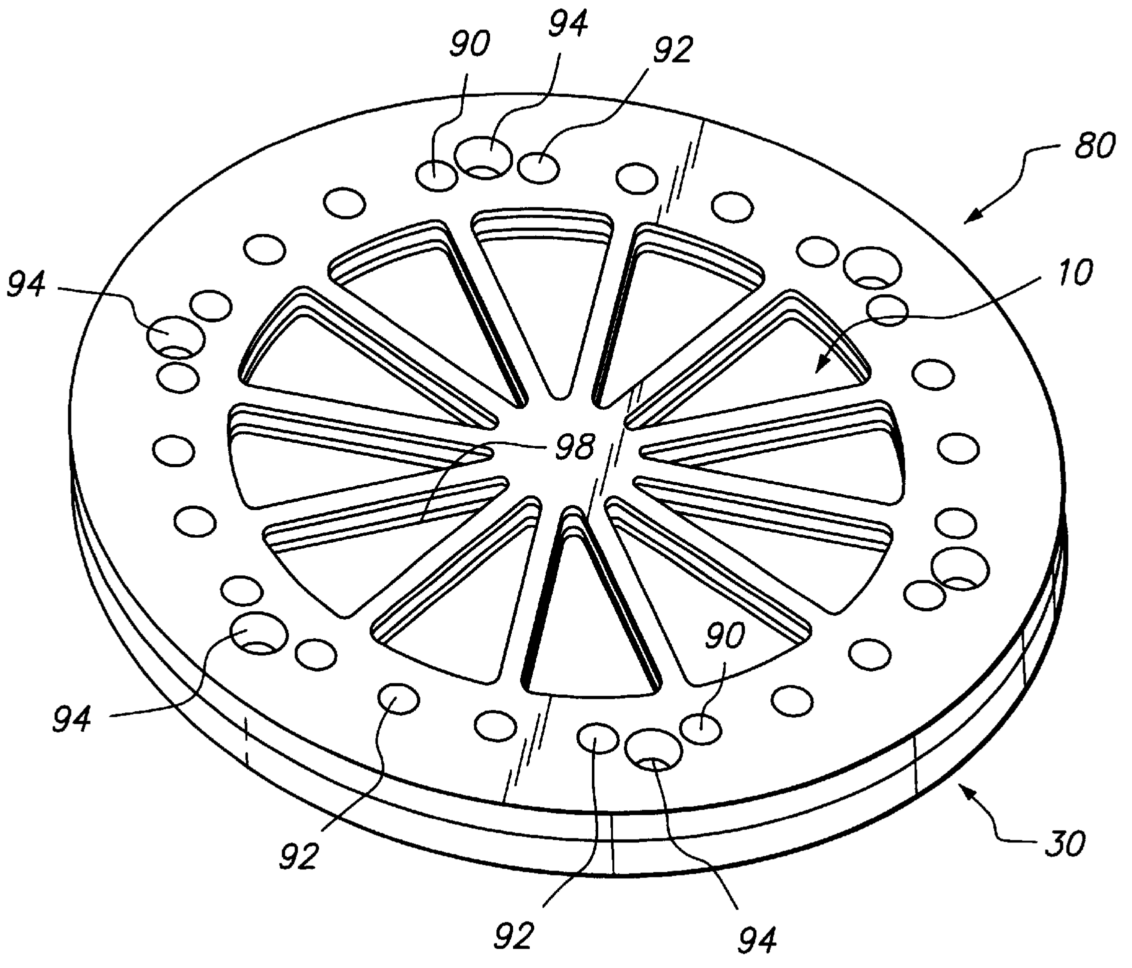
FIG. 4 is a perspective view of an embodiment of an apparatus of the present invention, assembled together with a substrate carrying multiple polynucleotide arrays.
Figure 5:
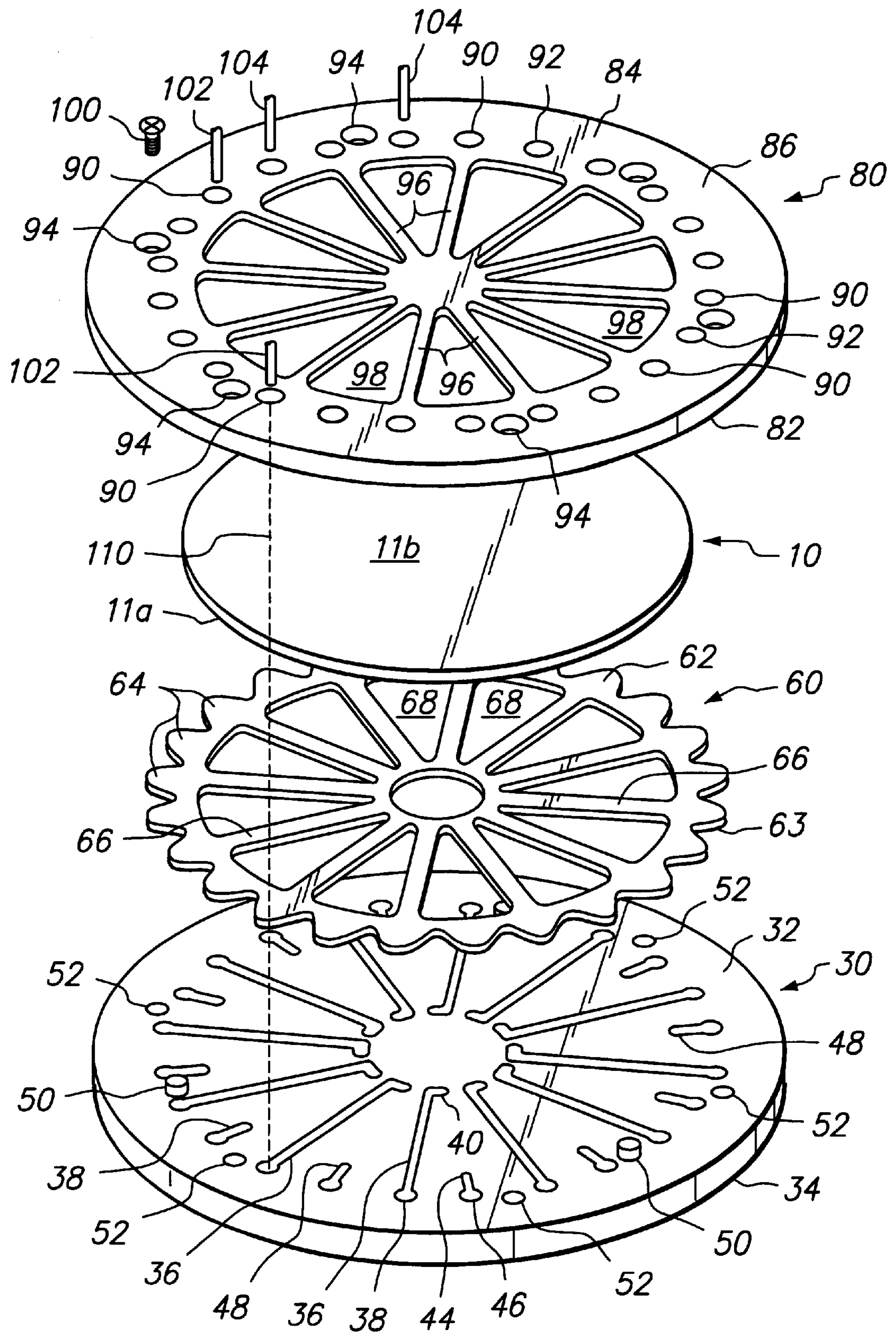
FIG. 5 is an exploded view of the components of FIG. 4.
Figure 6:
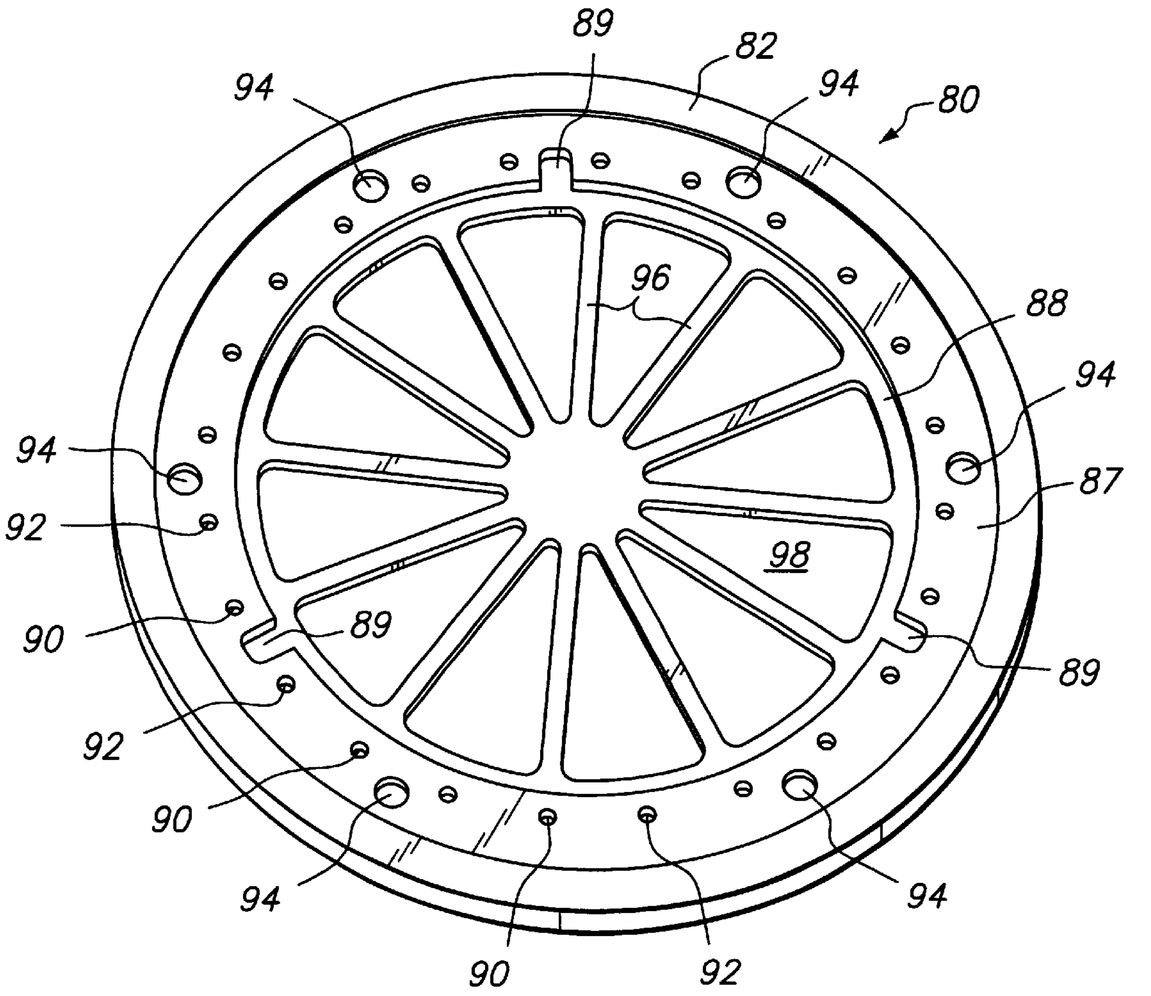
FIG. 6 is a view of the side of the cover facing the gasket.

Referring now to FIGS. 4 through 6, the illustrated apparatus may be used with a circular planar substrate 10 carrying twelve pie shaped arrays on a first side 11*a* of substrate 10. The apparatus includes a cover which includes a cover member 30 and a flat resilient gasket 60. Cover member 30 is a substantially flat contiguous plate with a second side 34, and with a first side 32 carrying fluid ducts in the form of a first set of channels 36 and a second set of channels 44. Channels 36 and 44 have slightly enlarged outer end portions 38, 46 respectively, while the first set of channels 36 also has a hooked inner end 40 as illustrated. Cover member 30 also carries three equally spaced studs 50 projecting from first side 32, as well as six threaded bores 52.

Gasket 60 has a first side 62 and a second side 63, and multiple pie-shaped openings 68 defined between ribs 66. Gasket 60 is designed to be sandwiched between substrate 10 and cover member 30 when the apparatus is assembled together with substrate 10 as shown in FIG. 4 and as most clearly illustrated in FIG. 5. Gasket 60 includes openings 68 which are dimensioned to be somewhat larger than, and to align with, respective pie-shaped arrays on the first side 11*a* of substrate 10. In this manner, cover member 30 and gasket 60 when assembled together with substrate 10, will define multiple, normally closed, chambers each containing a biopolymer array. Note that since substrate 10 and the first surface 32 of cover member 30 are substantially flat, the majority of the maximum thickness of such chamber (that is, the maximum distance between cover 30 and substrate 10 in such chamber excluding channels 36, 44), and in this case essentially all of the thickness, is defined by the thickness of gasket 60. Gasket 60 further includes port portions 64 at an outer periphery which port portions extend transversely beyond substrate 10 when the apparatus and substrate 10 are assembled together. Further, following assembly with substrate 10, port portions 64 are aligned with and lie over respective enlarged outer end portions 38, 46 of channels 36, 44 (thus, there are a total of twenty-four port portions 64 in the particular embodiment shown). Simultaneously, ribs 64 will lie over the remainder of each first channel 36, except for the hooked end inner ends 40 of channels 36 each of which will open into an innermost end of a corresponding chamber defined by the gasket openings 68. Similarly, each inner end 48 of the second set of channels 48 will open into an opposite, outermost end of a corresponding chamber. Thus, first channels 36 together with overlying port portions 64 will act as a first set of normally closed ports, while second channels 44 together with overlying port portions 64 will act as a second set of normally closed ports. In this manner, each chamber is accessed by a first and a second ports opening into opposite sides of the chamber, and both of which are normally closed by resilient port portions 64.

The apparatus further includes a coupler with a coupler member in the form of a plate 80 positional adjacent second side 11*b* of substrate 10, and six screws 100 (only one being shown in FIG. 5). Plate 80 has first and second sides 82, 86, respectively. Plate 80 is provided with six bores 94 which can be aligned with respective threaded bores 52 in cover member 30 when the apparatus is assembled with substrate 10. Six screws 100 (only one being shown in FIG. 5) together with bores 94 and threaded bores 52, act as an adjustable interconnect member in a manner that will shortly be described. Plate 80 includes first and second sets of guide openings 90, 92 respectively, which can be aligned with respective port portions 64 of gasket 60 when the apparatus is assembled. Ribs 96 of plate 80 define view openings 98 which align with respective arrays on substrate 10 and gasket openings 68 when the apparatus is assembled with substrate 10. Note that the first side 82 of plate 80 has a first recessed area 87 to receive gasket 60, as well as a further recessed second area 88 to receive substrate 10, as best seen in FIG. 6. This arrangement facilitates sealing of gasket 60 against substrate 10, while indents 89 receive studs 50 to align the assembly.

The apparatus of FIGS. 4 through 6 can be used by aligning the components and assembling them together with a substrate 10 as best illustrated particularly in FIG. 5 and described above. Note that when gasket 60 is aligned and positioned adjacent plate 30 to define the cover, openings 68 together with cover 30 at this point define multiple cavities with respective first and second ports communicating with the cavities. As already described, the ports include resilient self-sealing gasket port portions 64 normally closing the ports. This cover can then be assembled together with substrate 10 and plate 80 as already described. Note that studs 50 guide gasket 60 to aid in correctly registering it with respect to cover 30, by fitting in the gaps between adjacent gasket port portions 64. Studs 50 are also positioned to be just outside the perimeter of substrate 10, and therefore also help in guiding substrate 10 into correct registration with gasket 60. Screws 100 can be inserted through bores 94 and into aligned threaded bores 50 to urge the cover and substrate toward one another and retain them in the assembled position. In this manner, gasket 60 seals against cover member 30 and substrate 10 to define the normally closed chambers. However, different orders of assembly of the apparatus components can be envisaged in view of the above description.

Following assembly with a substrate 10, fluid samples can be introduced into respective chambers through one set of ports while venting through another set of ports. This can be done for each chamber in sequence or all chambers can be simultaneously loaded while venting. The introduction and venting can be accomplished using conduits in the form of first and second sets of hollow needles 102, 104 respectively (only some of which are shown in FIG. 5 for clarity). Each first needle 102 is guided by a guide opening 90 along the path illustrated by broken line 110. Specifically, each first needle 102 will be guided outside the perimeter of substrate 10 and penetrate a gasket port portion 64 from a first side 62 of gasket 60 to outer end 38 of a first channel 36 such that needle 102 is then in communication with an inner end of a chamber. Similarly, each second needle 104 will be guided outside the perimeter of substrate 10 and penetrate a gasket port portion 64 to an outer end 46 of a second channel 44 and is then in communication with an outer end of a chamber. Multiple fluid samples can then be introduced into respective chambers through normally closed portions of each, by injecting the sample with a slight pressure through one needle while venting is allowed to occur at the other. Alternatively, other means of establishing a pressure differential between a first and a second needle communicating with a given chamber, can be used to provide positive loading of samples into the chambers (for example, a slight vacuum could be applied to one needle). The self sealing construction of gasket port portions 64 avoids contamination during and after loading of chambers, and allows for the positive sample loading while avoiding sample losses. The presence of view openings 98 allows each chamber and the array in it, to be observed through the second side 11*b* of substrate 10 such that if there is a problem (such as a chamber being incompletely loaded with a sample) this can be observed.

Following loading of the chambers with samples, needles 102, 104 can be withdrawn and, due to the self-sealing nature of resilient gasket 60 and specifically port portions 64, the ports are retained closed. The apparatus can then be provided with a controlled set of conditions, such as an elevated temperature over a number of hours for polynucleotide hybridizations. The normally closed ports help avoid sample evaporation during such conditions while the coupler components described above help avoid any internally developed pressure from pushing cover member 30 and substrate 10 apart (which could result in sample leakage). When controlled conditions have been completed, sample can be positively withdrawn using a first and second set of needles 102, 104 in a manner similar to loading, except a negative pressure differential is applied between needles communicating with each chamber, to cause sample removal out through one of the sets of needles 102, 104. Each array 12 can then be rinsed by introducing rinse solution (such as a buffer solution) into the chambers through one set of needles while venting through the other set. The apparatus can be disassembled from substrate 10 and the binding pattern of the arrays on substrate 10 observed (such as by observing fluorescence in the case where a sample was labeled with a fluorescent label). Note that gasket 60 is not adhered to cover member 30 such that during disassembly, following detachment of the cover from substrate 10, gasket 60 freely detaches from cover member 30. This allows the components to be readily cleaned and also allows relatively inexpensive gasket 30 to be disposed of if desired, while the other components may be re-used. Also, it will be appreciated that during re-use the volume of the chambers can be readily altered simply by using a gasket of the same shape but of a different thickness.

Figure 7:
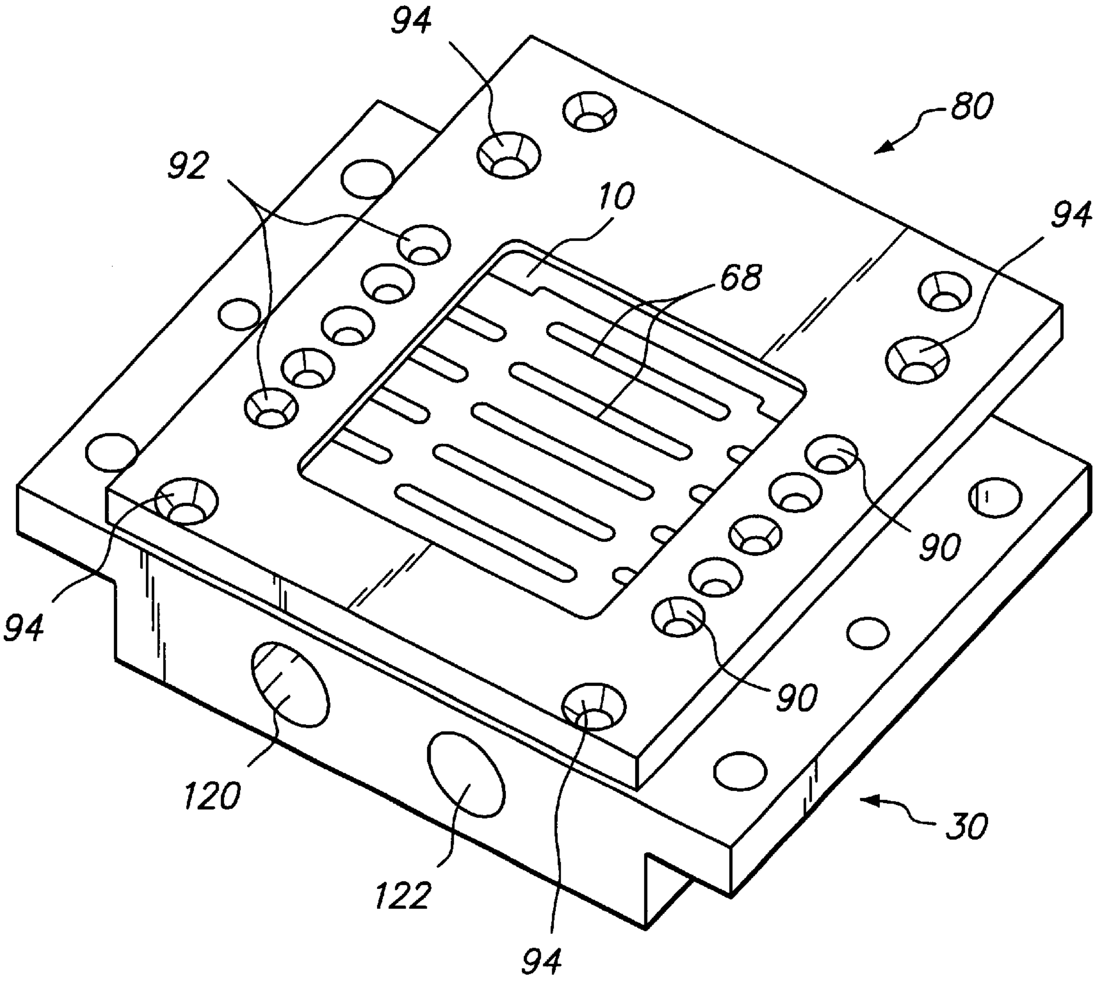
FIG. 7 is a perspective view of another embodiment of an apparatus of the present invention, assembled together with a substrate carrying multiple polynucleotide arrays.
Figure 8:
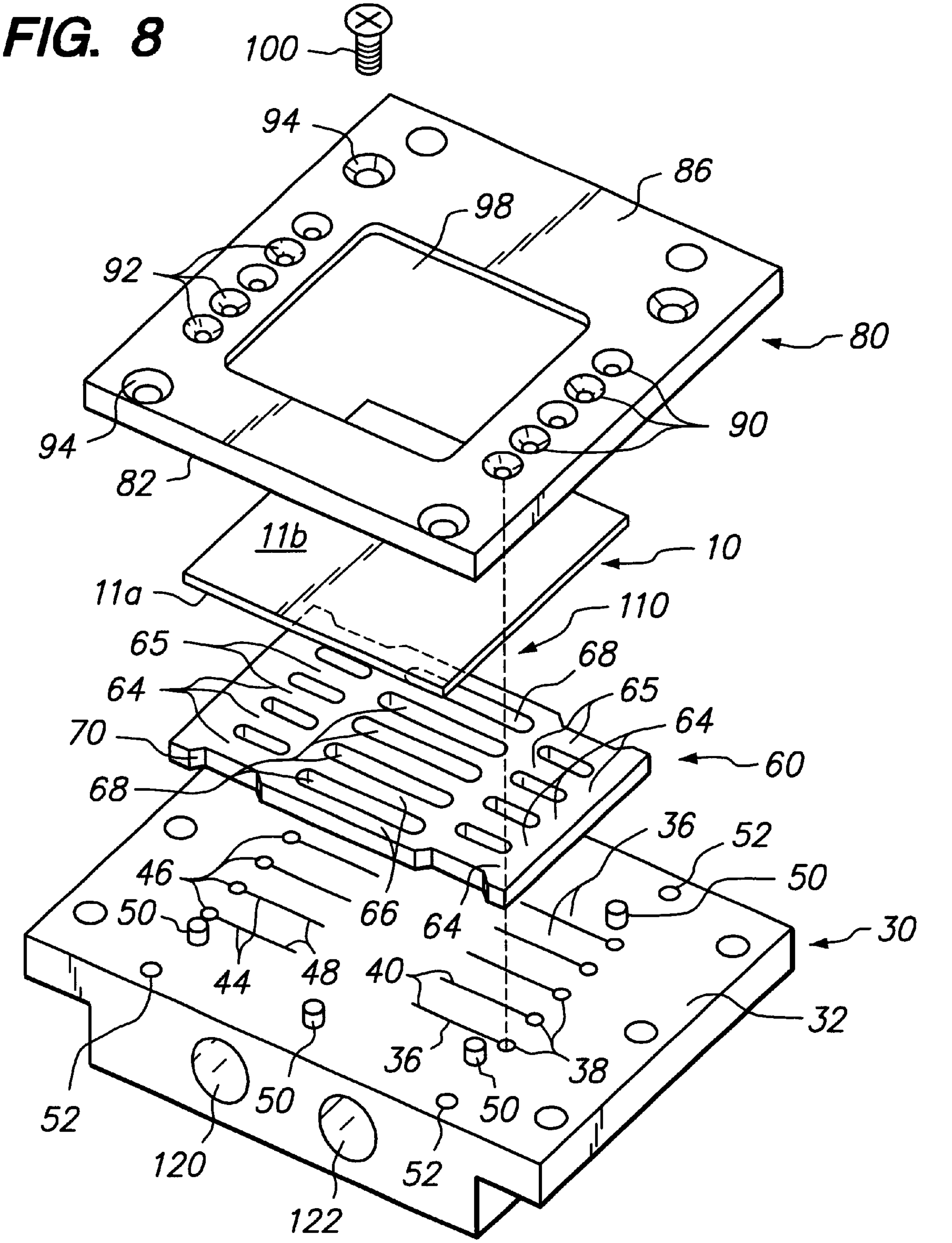
FIG. 8 is an exploded view of the components of FIG. 7.
Figure 9:
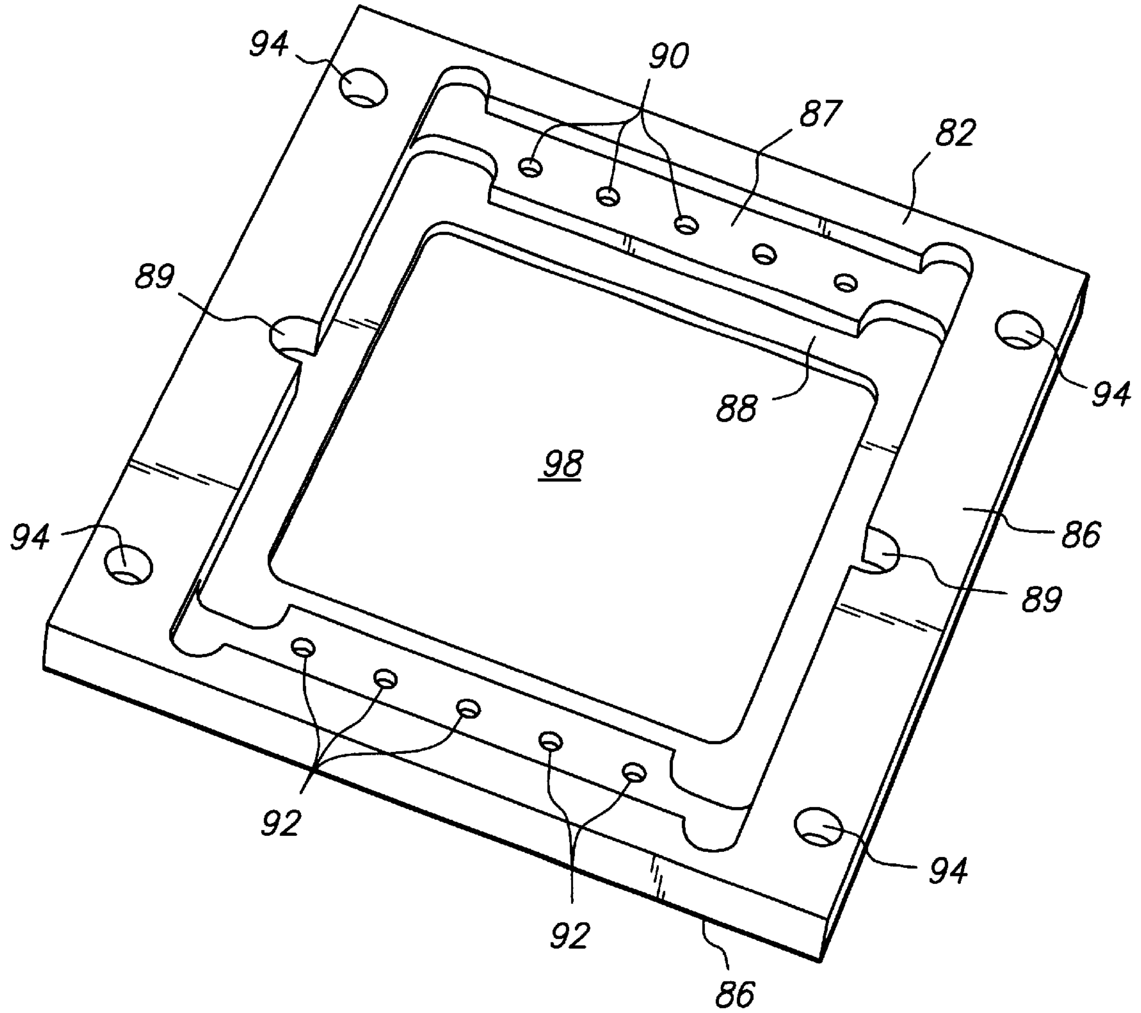
FIG. 9 is a view of the side of the cover facing the gasket.
Figure 10:
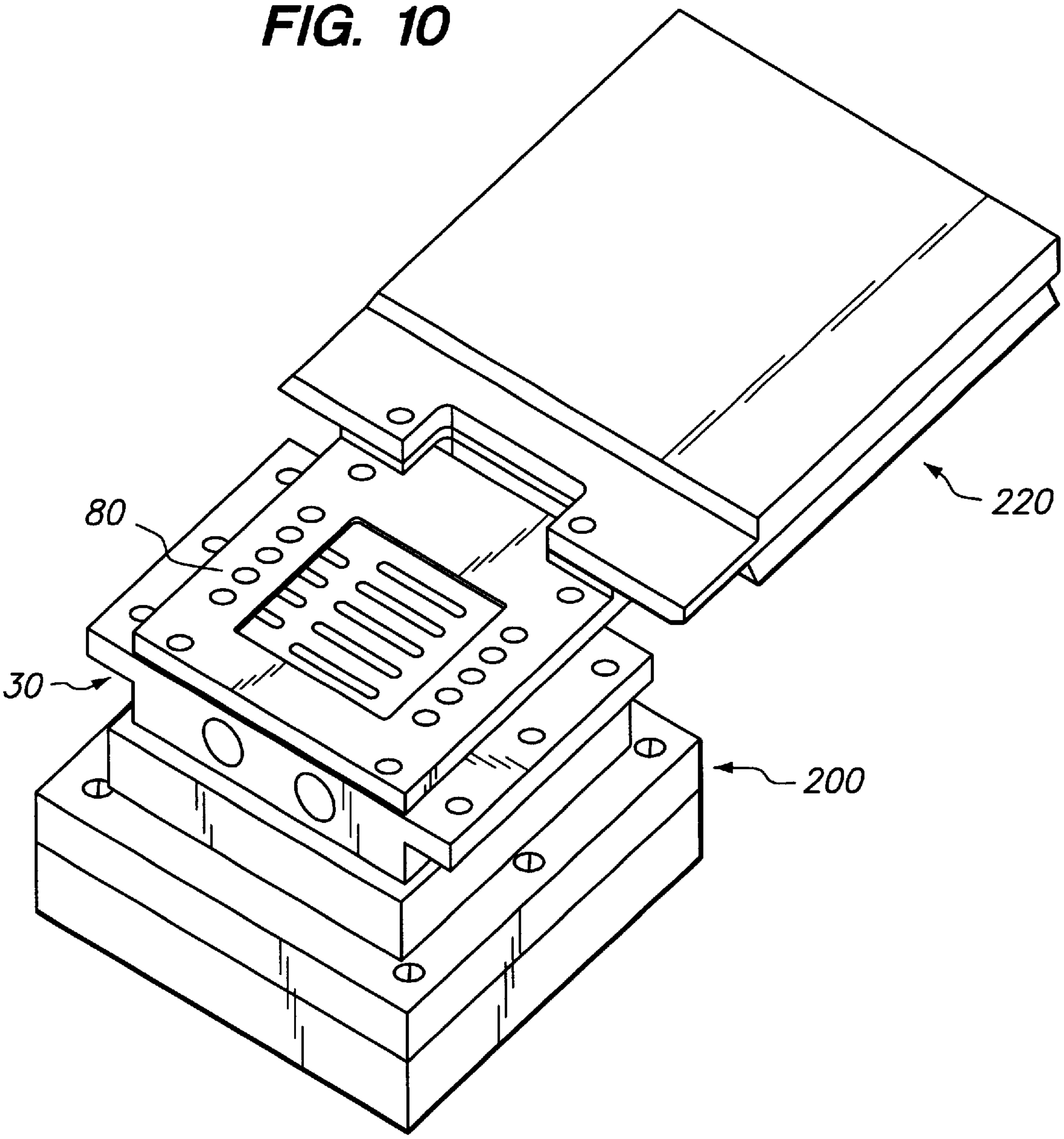
FIG. 10 illustrates the assembly of FIG. 7 positioned in a heating block.

The embodiment of the apparatus of FIGS. 7 through 9 is essentially similar to, and is used in an analogous manner, to the embodiment of FIGS. 4 and 5 as already described. Again, the same reference numbers have been used to indicate similar parts. However, the embodiment of FIGS. 7 through 9 is adapted for use with a rectangular substrate carrying five, substantially rectangular arrays. In this embodiment then, first and second channels 36, 44 are positioned beneath ribs 65 of gasket 60, with inner ends 40, 46 opening into opposite ends of the chambers defined in part by gasket openings 68. Further, cover 30 is provided with bores 120, 122 into which probes for monitoring conditions can be inserted. Note how the four guide pins 50 are positioned to abut against shoulders 70 of gasket 60, as well as the perimeter of substrate 10, to aid in correctly positioning both during assembly. FIG. 10 illustrates enclosing the assembled apparatus and substrate in FIG. 8, in a suitable heating block 200 and cover 220.

Figure 11:
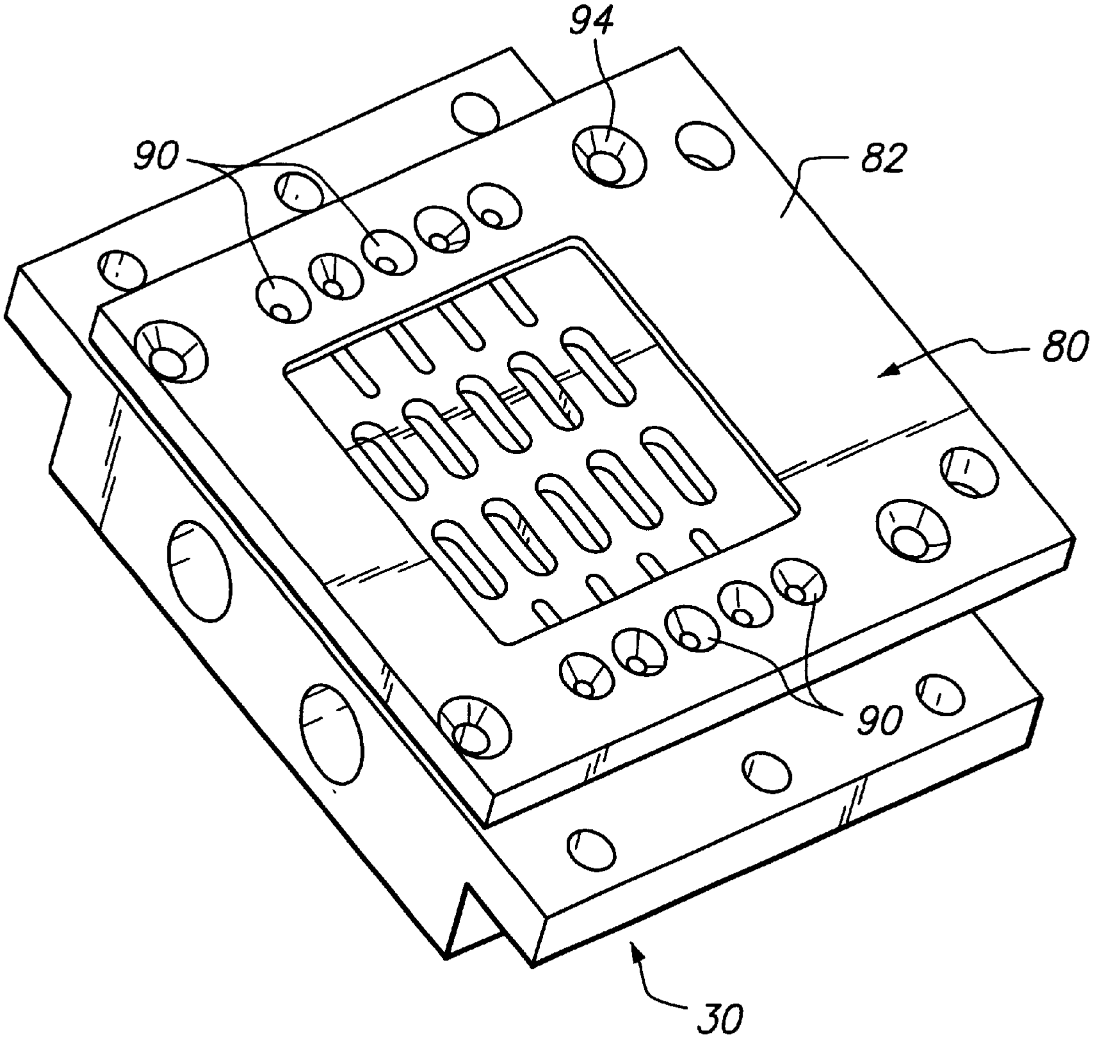
FIG. 11 is a perspective view of a further embodiment of an apparatus of the present invention, assembled together with a substrate carrying multiple polynucleotide arrays.
Figure 12:
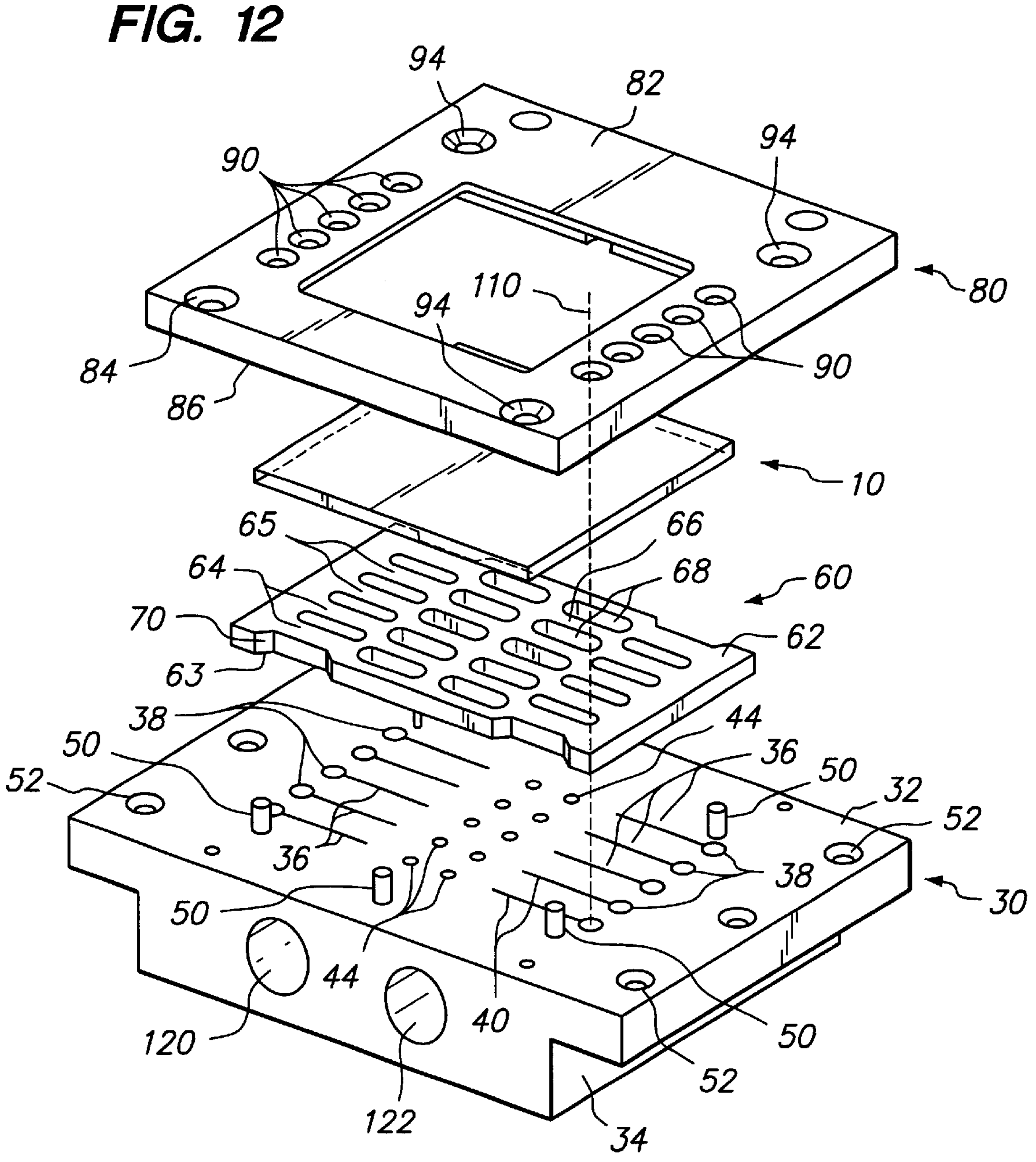
FIG. 12 is an exploded view of the components of FIG. 11.
Figure 13:
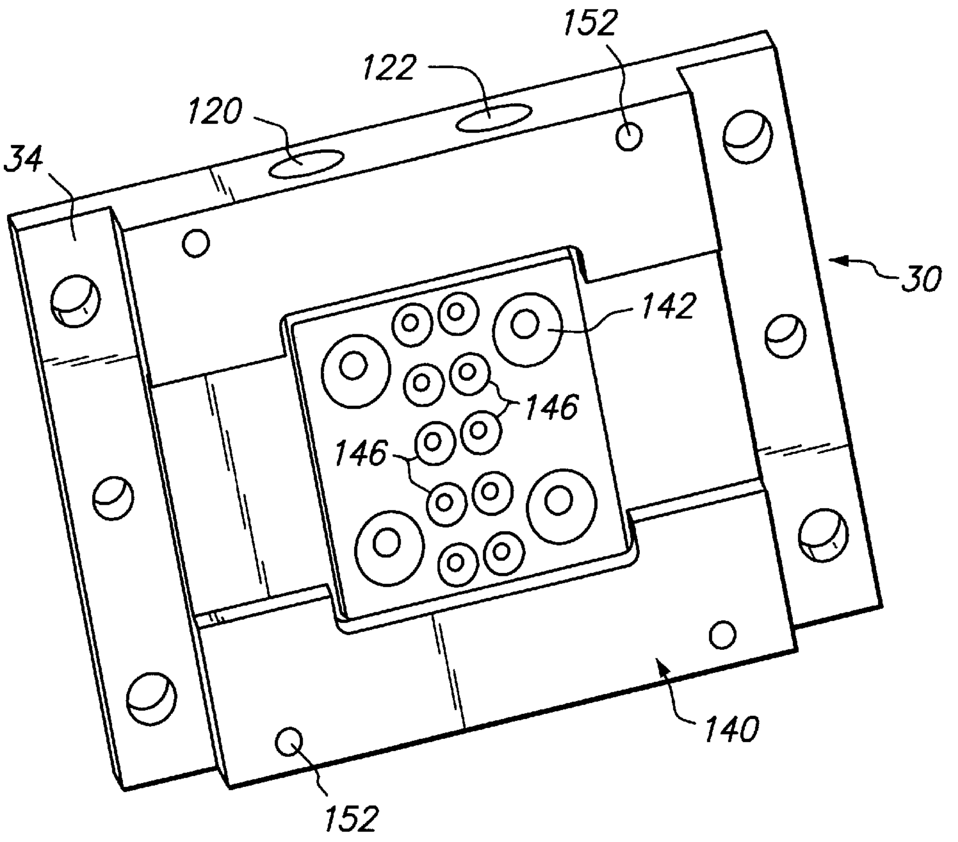
FIG. 13 is a bottom view of the assembly of FIG. 11.

The embodiment of FIGS. 11 and 12 is similar to that of FIGS. 7 through 9, except the apparatus is adapted for use with a square substrate carrying ten arrays. Again, similar components are numbered the same and the apparatus is used in an analogous manner. However, in this embodiment the ten first channels 36 are provided in two sets of five on opposite sides of the upper surface 32 of cover member 30. Cover member 30 is provided with conduits in the form of openings 44. These openings 44 are alignable with guide openings 146 in an additional plate 140. Plate 140 can be clamped to cover member 30 by means of threaded screws (not shown) passing through bores 152 and into aligned threaded bores in second surface 34 of cover member 30. A flat, resilient second gasket is clamped between them to provide the resilient self-sealing portions of the second ports. In use the second set of needles may be guided through openings 146 through the second gasket and into openings 44 to communicate with each of the ten chambers.

Figure 14:
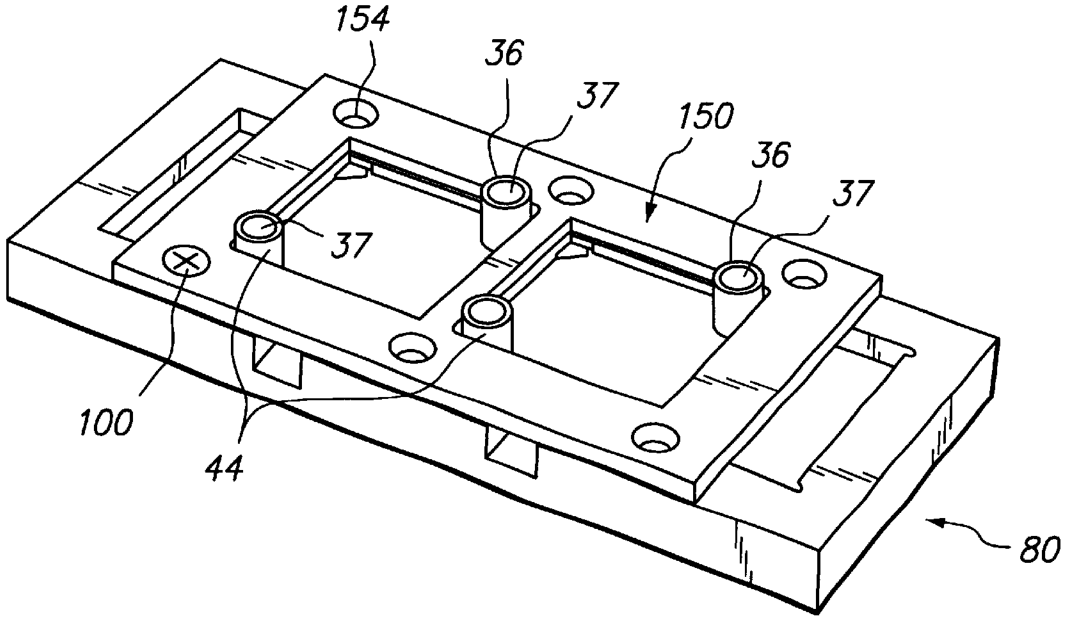
FIG. 14 is a perspective view of a still further embodiment of an apparatus of the present invention, assembled together with a substrate carrying multiple polynucleotide arrays.
Figure 15:
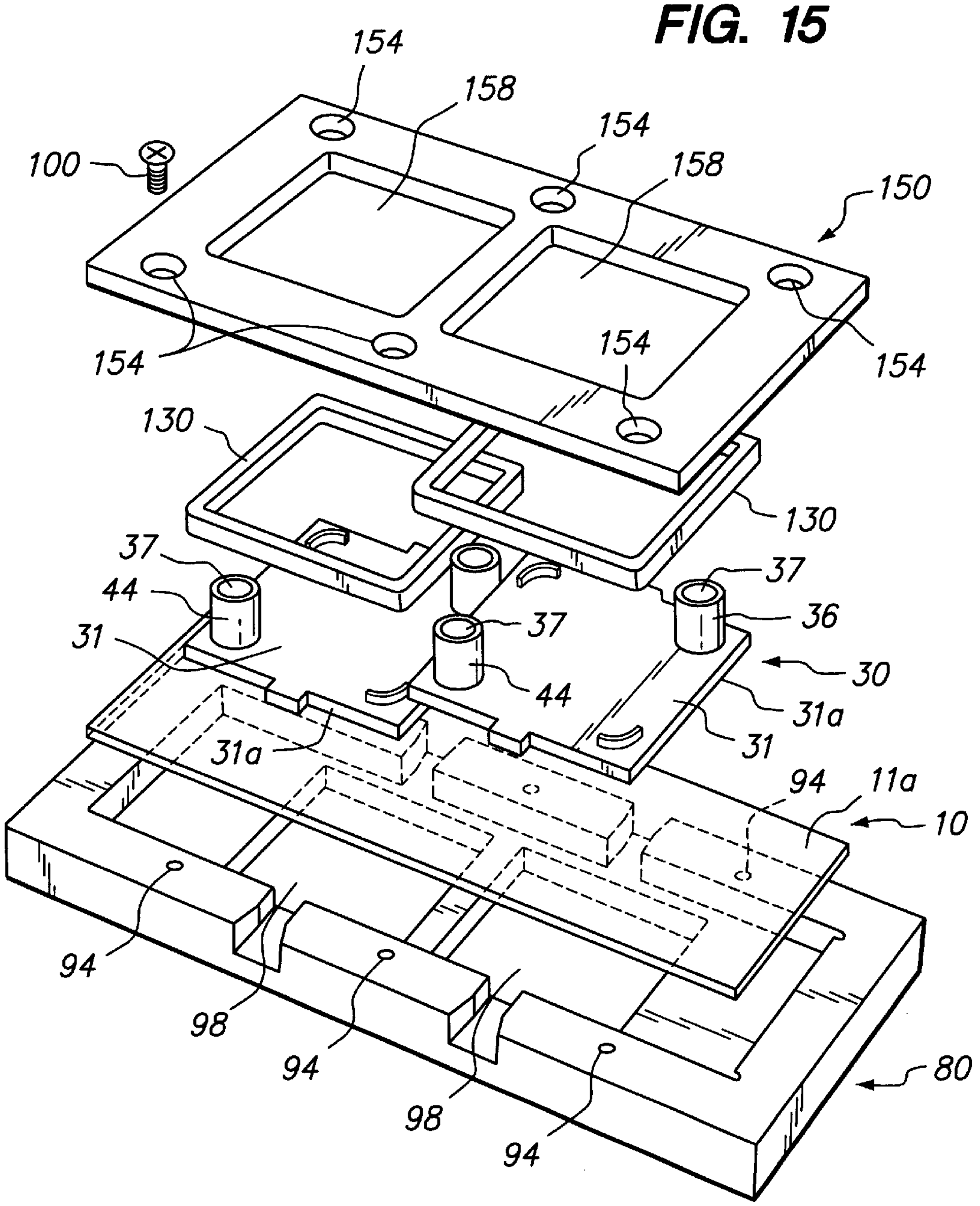
FIG. 15 is an exploded view of the assembly of FIG. 14.

The embodiment of the apparatus of FIGS. 14 and 15 is adapted for use with a rectangular substrate 10 having two arrays on a first side 11*a*. The illustrated cover in the present case is formed only from a cover member which is not contiguous but includes two independent sections 31. However, the cover can be molded with both sections 31 as one contiguous piece. Each section 31 carries first port and second ports, which include conduits 36, 44 respectively. Each of the first and second ports are normally closed by a resilient self-sealing port portion in the form of septum 37. In this embodiment no gasket 60, present in the previously described embodiments, is used which is sandwiched between substrate 10 and the cover member 30. Instead, each section 31 is made of plastic which is sufficiently flexible about its perimeter 31*a* as to form a liquid tight seal when pressed against the first side 11*a* of substrate 10 to form a chamber containing a corresponding one of the two arrays. The clamp in this embodiment includes the plate 80 with threaded bores 94 and six threaded screws 100 (only one of which is shown in FIG. 15), and further includes a cover backing plate 150 and resilient spacers 130. Plate 150 includes bores 154 for screws 100 and two openings 158 such that the majority of the force supplied by tightening screws 100, will be applied through spacers 130 to the perimeters 31*a* of cover member sections 31, to aid in establishing the seal of perimeters 31*a* against substrate 10. The remainder of the components of this embodiment are similar to those described above and again, like numbers have been used to indicate similar parts. This embodiment may also used in a manner analogous to that described above in connection with the other embodiments.

Figure 16:
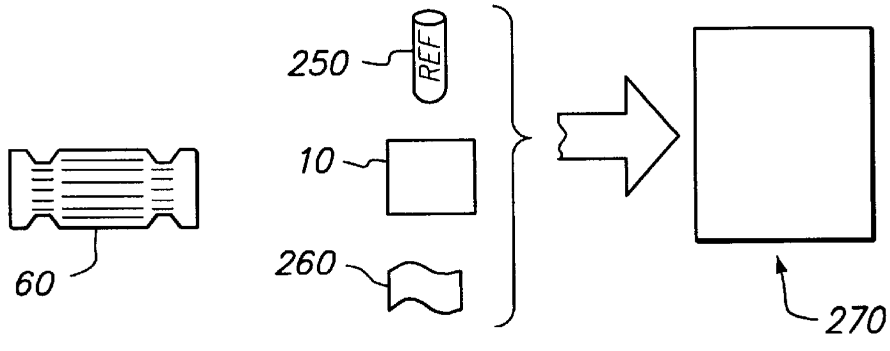
FIG. 16 illustrates a kit of the present invention.

FIG. 16 illustrates a kit of the present invention which may be assembled by a manufacturer. The illustrated kit includes a contiguous substrate 10 carrying multiple arrays of biopolymers linked to the substrate (such as polynucleotide arrays). A gasket 60 is provided which has openings 68 alignable with respective arrays on substrate 10. Note that gasket 60 is not adhered to any cover (no rigid member covering gasket openings 68 is adhered to gasket 60). The kit may also include a reference sample 250 in a suitable reference sample container. Reference sample 250 may contain one or more (mixed or separate) components which will interact with an array in a reproducible known manner under a predetermined set of conditions, and which interaction may vary depending on conditions. For example, when array 10 carries multiple polynucleotide arrays the reference sample may be one or more polynucleotides (mixed or separate) selected to hybridize with array regions in an expected pattern (which includes location and degree of hybridization). Data on one or more characteristics of the expected pattern can be provided to an end user remote from the manufacturer on a medium 260 of the kit, which medium 260 may also carry instructions on using the reference sample as a reference. Such instructions may provide (by explicitly stating) that the reference sample is to be exposed to at least one array on substrate 10 in the same kit, and more explicitly that the reference sample is to be exposed to at least one array under the same set of conditions as at least one test sample being exposed to another array on the same substrate. The instructions may further provide that an array to which the reference sample is exposed, is not to be exposed to a sample to be tested. Medium 260 may carry the expected pattern characteristics and instructions as machine (for example, a suitably programmed computer with suitable peripherals) and/or human readable characters, or any combination of the foregoing, and thus may, for example, be paper, cardboard, or a portable optical or magnetic recording medium. All of the kit components may be provided in a single container 270 of any suitable construction, and the resulting kit may be shipped from the manufacturer to a remote user.

The kit of FIG. 16 may include only combinations of any two or three of the components illustrated. For example, the kit may omit reference sample 250 and/or gasket 60, or alternatively may omit gasket 60 and/or medium 260.

When an end user receives the kit of FIG. 16, it is used by assembling gasket 60 together with substrate 10 and a suitable apparatus of the present invention (for example, the apparatus of FIGS. 7 and 8). The user may follow instructions on medium 260 and expose at least one (and more typically, multiple ones) of the arrays on substrate 10 to a test sample or samples, under a first set of conditions and expose (for example, simultaneously) at least one of the arrays to the reference sample 250 under the same set of conditions. In particular, the test samples and reference sample 250 may simultaneously be introduced into respective chambers of the assembled apparatus. The resulting binding pattern may then be observed in a manner as already described. If the observed binding pattern for the reference 250 exhibits one or more characteristics which are outside one or more predetermined limits (for example, an observed fluorescence signal from one spot is outside a predetermined value), the results for the test samples may be rejected as being unreliable. Alternatively, whether or not the observed binding pattern for the reference 250 exhibits one or more characteristics which are outside one or more predetermined limits, the observed binding pattern results for the test samples may be modified (typically during data processing) based on the difference or differences between one or more expected and observed characteristics of an array exposed to the reference sample.

Most of the components of the embodiments of the apparatus of the embodiments of FIGS. 4–11 described above, may be made of metal, with the exception of the gaskets which may be made of any suitable rubber or thermoplastic elastomer. Potentially suitable rubbers include butyl rubber, nitrile, silicone, ethylene propylene ("EDPM"), neoprene, polyacrylate, and the like. Potentially suitable thermoplastic elastomers include SANTOPRENE and TREFSIN (both available from Advanced Elastomer Systems, Akron, Ohio), and the like. Substrate 10 may be of any suitable material (often, but not necessarily, a transparent material), such as glass, fused silica, silicon, plastic or other materials. In the embodiment of FIGS. 14 and 15, the sections 31 may also be made of a plastic such as polypropylene, polyethylene or acrylonitrile-butadiene-styrene ("ABS"). Further details on the construction of the embodiment of FIGS. 14 and 15 can be found in co-pending U.S. patent application entitled "APPARATUS AND METHOD FOR CONDUCTING CHEMICAL OR BIOCHEMICAL REACTIONS ON A SOLID SURFACE WITHIN AN ENCLOSED CHAMBER" by Carol Schembri et al., assigned to the same assignee of the present application Ser. No. 09/343,372 and filed on the same date as the present application. That application and all other references cited in the present application, are incorporated herein by reference.

Modifications in the particular embodiments described above are, of course, possible. For example, where a pattern of arrays is desired, any of a variety of geometries may be constructed other than the organized rows and columns of arrays 12 of FIG. 1. For example, arrays 12 can be arranged in a series of curvilinear rows across the substrate surface (for example, a series of concentric circles or semi-circles of spots), and the like. Similarly, the pattern of regions 16 may be varied from the organized rows and columns of spots in FIG. 2 to include, for example, a series of curvilinear rows across the substrate surface(for example, a series of concentric circles or semi-circles of spots), and the like. Even irregular arrangements of the arrays or the regions within them can be used, at least when some means is provided such that during their use the locations of regions of particular characteristics can be determined (for example, a map of the regions is provided to the end user with the array).

The present methods and apparatus may be used to deposit biopolymers or other moieties on surfaces of any of a variety of different substrates, including both flexible and rigid substrates. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used, particularly when such are cut after fabrication into smaller size substrates carrying a smaller total number of arrays 12. Substrates of other configurations and equivalent areas can be chosen. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties is deposited may be smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), Various modifications to the embodiments of the particular embodiments described above are, of course, possible. Accordingly, the present invention is not limited to the particular embodiments described in detail above.

What is claimed is:

1. A method of testing multiple fluid samples with multiple biopolymer arrays to detect a binding pattern between the multiple fluid samples and the arrays, comprising:

(a) assembling a cover to a one-piece substrate carrying on a first side, multiple arrays each with multiple regions of biopolymers linked to the substrate, such that the cover an the substrate together form a plurality of chambers each containing a biopolymer array and each being accessible through its own port which includes a resilient self-sealing portion;

(b) introducing the multiple fluid samples into respective chambers through a port of each such that the fluid samples contact respective arrays; and (c) observing a binding pattern on the arrays;

wherein each chamber is accessible through a first and a second port each of which includes a resilient self-sealing portion, the method additionally comprising inserting a first set of conduits through the resilient members of respective first ports, and inserting a second set of conduits through the self-sealing portion of respective second ports, and wherein the multiple fluid samples are introduced into each chamber through the first set of conduits while venting occurs through the second set of conduits.

2. A method according to claim 1 wherein the assembling includes applying an external force to urge the cover toward the substrate and which remains applied to retain them in the assembled position.

3. A method according to claim 1 wherein fluid samples are simultaneously introduced into each chamber through the first set of conduits.

4. A method according to claim 2 wherein the force is applied from a coupler extending between the cover and the substrate to urge the cover toward the substrate and retain them in the assembled position.

5. A method according to claim 4 wherein the coupler includes a plate with at least one view opening and includes an adjustable interconnect member, and wherein the coupler application comprises:

positioning the plate facing a second side of the substrate with the at least one view opening in alignment with the arrays such that the arrays can be observed from the second side of the substrate through the at least one plate view opening;

extending the adjustable interconnect member between the cover and the plate; and adjusting the interconnect member to urge the cover toward the substrate.

6. A method according to claim 4 additionally comprising, after applying the coupler, heating the chambers.

7. A method of testing multiple fluid samples with multiple biopolymer arrays to detect a binding pattern between the multiple fluid samples and the arrays, comprising:

(a) assembling a cover to a contiguous substrate carrying on a first side, multiple arrays each with multiple regions of biopolymers linked to the substrate, such that the cover and the substrate together form a plurality of chambers each containing a biopolymer array and each being accessible through its own port;

(b) introducing the multiple fluid samples into respective chambers through a port of each such that the fluid samples contact respective arrays; and (c) observing a binding pattern of the arrays;

wherein each chamber is accessible through a first and a second port, and wherein fluid samples are introduced into respective chambers through respective first ports while venting through respective second ports.

8. A method according to claim 7 wherein the maximum distance between the substrate and the cover in the chambers is no greater than 2 mm.

9. A method according to claim 7 wherein each of the chambers has a volume no greater than 1000 $\mu$l.

10. A method according to claim 7 wherein the multiple fluid samples are different fluid samples.

11. A method of testing multiple fluid samples with multiple biopolymer arrays to detect a binding pattern between the multiple fluid samples and the arrays, using a cover which includes a cover member and a resilient gasket with multiple openings, the method comprising:

(a) assembling the cover to a contiguous substrate carrying on a first side multiple arrays each with multiple regions of biopolymers linked to the substrate, with the gasket sandwiched between the substrate and cover member and the gasket openings aligned with respective arrays, such that the cover and the substrate together form a plurality of chambers each containing a biopolymer array and being accessible through a port comprising respective port portions of the resilient gasket which normally close the port;

(b) penetrating gasket port portions with at least one conduit and introducing fluid samples into respective chambers through the at least one conduit and chamber ports such that the fluid samples contact respective arrays; and (c) observing a binding pattern of the arrays.

12. A method according to claim 11 wherein, following assembly, the gasket has a first side facing the substrate and a second side facing the cover member, and has port portions positioned transversely beyond the substrate, and wherein the ports further comprise respective fluid ducts in the cover member communicating between respective chambers and respective port portions of the gasket such that the chambers can be accessed by conduits which have penetrated from the first side of the gasket through the port portions to the ducts.

13. A method according to claim 12 wherein the ducts are channels in a first side of the cover member which faces the gasket.

14. A method according to claim 12 wherein each chamber has a first and a second port, the method additionally comprising inserting a first set of conduits through the gasket port portions of respective first ports, and inserting a second set of conduits through the gasket port portions of respective second ports, and wherein the multiple fluid samples are introduced into each chamber through the first set of conduits while venting occurs through the second set of conduits.

15. A method according to claim 13 additionally comprising applying a coupler extending between the cover and the substrate to urge the cover toward the substrate and retain them in the assembled position, the coupler including a first member which is positioned adjacent a second side of the substrate and an adjustable interconnect member extending between the first member and the substrate.

16. A method according to claim 15 wherein the first member comprises a plate having guide openings which, following application of the coupler, are aligned with respective port portions of the gasket.

17. A method according to claim 16 wherein the plate has at least one view opening and wherein the coupler member application comprises positioning the plate facing a second side of the substrate with the at least one view opening in alignment with the arrays such that the arrays can be observed from the second side of the substrate through the at least one view opening.

18. An apparatus for testing multiple fluid samples with multiple biopolymer arrays, comprising:

(a) a cover defining multiple cavities on a first side and with respective ports communicating with the cavities, the ports including respective resilient self-sealing portions normally closing the ports, which cover can be assembled to a one-piece planar substrate carrying on a first side, multiple arrays each with multiple regions of biopolymers linked to the substrate, such that the cover and the substrate together form a plurality of chambers each containing a biopolymer array;

wherein the cover has a first and a second set of ports such that each chamber is accessible through a first and a second port so that fluid samples can be introduced into respective chambers through respective first ports while venting through respective second ports.

19. An apparatus according to claim 18 additionally comprising the planar substrate attached to the cover.

20. An apparatus for testing multiple fluid samples with multiple biopolymer arrays, comprising:

a cover including: a resilient gasket with multiple openings and port portions; and a cover member wherein the gasket and cover member are dimensioned so that the cover can be assembled to a contiguous planar substrate carrying on a first side multiple arrays each with multiple regions of biopolymers linked to the substrate, with the gasket sandwiched between the substrate and cover member and with the gasket openings aligned with respective arrays, such that the cover and the substrate together form a plurality of chambers each containing a biopolymer array and each accessible through a port which includes the gasket port portions normally closing the port, upon penetration of a conduit through respective port portions of the resilient gasket.

21. An apparatus according to claim 20 wherein:

the gasket is dimensioned such that, following assembly, a first side of the gasket faces the substrate and a second side of the gasket faces the cover member, and the port portions are positioned transversely beyond the substrate;

and wherein the ports further comprise respective fluid ducts in the cover member which, following assembly, communicate between respective chambers and respective port portions of the gasket such that the chambers can be accessed by conduits which have penetrated from the first side of the gasket through the port portions thereof to the ducts.

22. An apparatus according to claim 21 wherein the ducts are channels in a first side of the cover member which faces the gasket following assembly.

23. An apparatus according to claim 21 wherein the cover member and gasket have ducts and port portions, respectively, such that following assembly each chamber has a first and a second port both normally closed by a gasket port portion.

24. An apparatus according to claim 21 additionally comprising a coupler to extend between the assembled cover and substrate to urge the cover toward the substrate and retain them in the assembled position, the coupler including a first member positionable adjacent a second side of the substrate and an adjustable interconnect member extendable between the first member and the substrate.

25. An apparatus according to claim 24 wherein the first member comprises a plate having guide openings alignable with respective port portions of the gasket.

26. An apparatus according to claim 24 wherein the plate has at least one view opening through which the arrays can be observed when the plate faces a second side of the substrate with the coupler retaining the cover and substrate in the assembled position.

* * * * *